United States Patent [19]
DiMatteo

[11] Patent Number: 5,479,942
[45] Date of Patent: Jan. 2, 1996

[54] ATHLETIC PROTECTIVE SYSTEM

[76] Inventor: Frank DiMatteo, 501 Sunnyfield Dr., Monroeville, Pa. 15146

[21] Appl. No.: 308,602

[22] Filed: Nov. 9, 1994

[51] Int. Cl.$^6$ .............................. A61F 5/37; A61F 13/00
[52] U.S. Cl. .............................. 128/846; 602/67; 602/68
[58] Field of Search .................... 602/67, 68, 69, 602/70, 71, 72, 73; 128/891, 98.1, 105.1, 95.1, 96.1

[56] References Cited

U.S. PATENT DOCUMENTS

| | | | |
|---|---|---|---|
| 849,471 | 4/1907 | Gamble | 602/72 |
| 903,472 | 11/1908 | Huddleston | 602/73 |
| 1,421,077 | 6/1922 | Goldsmith | 602/71 |
| 2,033,551 | 3/1936 | Rumery | 602/73 |
| 2,266,062 | 12/1941 | Montmarquet | 602/72 |
| 2,283,684 | 5/1942 | Matthews | 602/72 |
| 2,427,428 | 9/1947 | Vitale | 602/72 |
| 2,686,517 | 8/1954 | Boyd | 602/72 |
| 4,257,414 | 3/1981 | Gamm | 602/72 |
| 4,453,541 | 6/1984 | Castelli | 602/72 |

Primary Examiner—Michael A. Brown
Attorney, Agent, or Firm—James Ray & Associates

[57] ABSTRACT

A system for protecting a male genital region from injury including a cup having a rearwardly extending lower portion to extend between the upper thighs and engage the body proximate to the superior ramii, the inferior ramii, and the Ischial ramii of the pelvis with minimal contact with the upper thighs, and a cup periphery having a generally curved upper edge adapted to arcuately contact the wearer's abdomen above the pubic area, and a generally circular side edge periphery at a mid-section below the generally curved upper edge adapted to enclose the wearer's genitals without crowding, and in addition, a cup supporter having an elastic waist band with a fabric pouch attached at the front to contain the cup, and having a pair of elastic leg straps extending from the lower end of the pouch and back to the front of the waist band, with a pair of elastic support straps extending from the mid-length of the leg straps to the back side of the waist band.

20 Claims, 4 Drawing Sheets

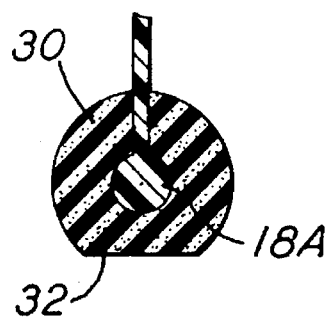
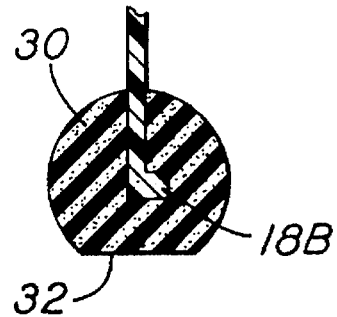
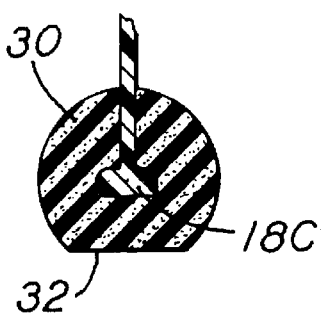
FIG. 7   FIG. 8   FIG. 9
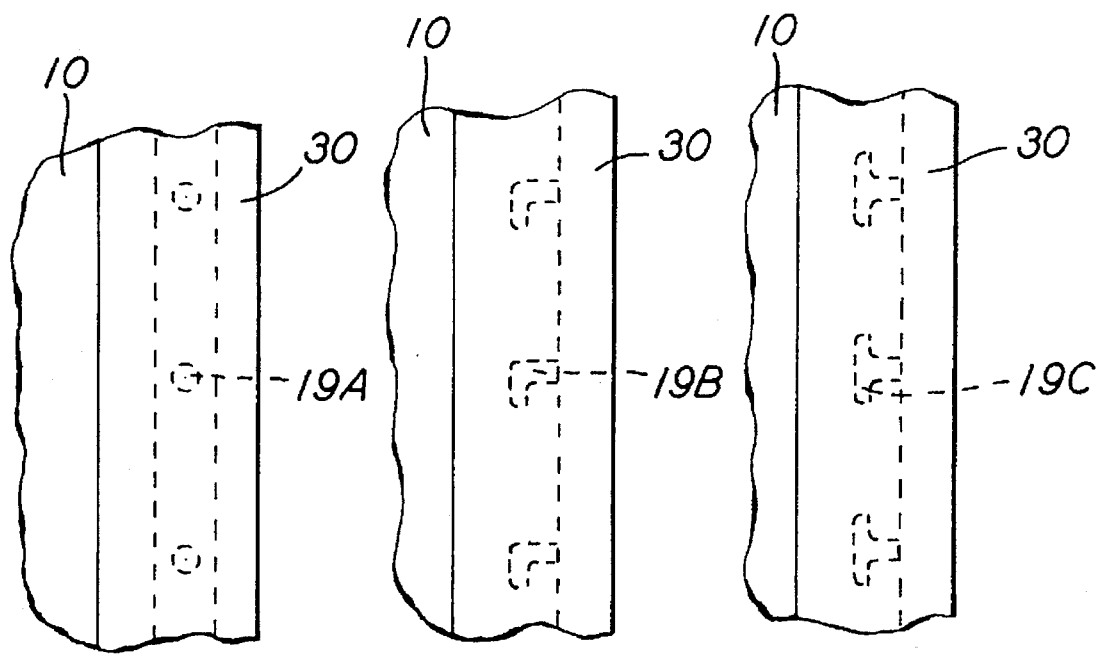
FIG. 10   FIG. 11   FIG. 12

ATHLETIC PROTECTIVE SYSTEM

FIELD OF THE INVENTION

This invention relates generally to protective devices, and more particularly to an improved system for protecting the male groin region, particularly during athletic competition, which affords better protection and improved comfort in comparison to systems of the prior art. The system of this invention includes a protective cup having a new and improved geometry that affords better protection and improved comfort, and a new and improved cup supporter that better retains the cup to stabilize its proper position and reduces the possibility for having the cup moved as a result of blows thereto.

BACKGROUND OF THE INVENTION

Cups and other devices for the protection of the male groin region are well known and extensively utilized, particularly for protection during athletic competition. Generally, these devices are limited to the "jockstrap" or athletic supporter, which is an elastic-fabric garment used to support the male genitals, and to the "cup", which is a rigid cup-like enclosure normally positioned within a pouch of a specially designed jockstrap type of athletic supporter, and is intended to physically shield the genitals from physical impact. Such cups normally define a cavity area which is designed to encase the male genitals, and a resilient rubber covered edge portion surrounding the cavity, intended to fit against the abdomen around the genitals, which transfers any impact forces on the cup to the abdomen. While the use of an athletic supporter or jockstrap alone may be adequate protection for some athletic activities, such as swimming, field and track events and other non-contact sports, it is most common to wear a cup during athletic activities such as football, hockey, rugby, soccer, and other such contact sports activities to protect the male genitals from injury as the result of inadvertent physical blows to the groin region. While such cups are most commonly worn during athletic competition, it should be appreciated that workers sometimes find it necessary to wear such cups in certain occupations where physical blows to the groin region can be expected.

During athletic competition, most such inadvertent blows to the groin region are directed perpendicular to the axis of the body (i.e., the spine) so that the cup directly absorbs the force of the blow to shield the genitals from such a blow as intended. As many athletes have experienced, however, many such inadvertent blow to the genital area my be directed generally upward, or angularly upward, somewhat parallel to the axis of the body, which can cause many of the prior art cups to be pushed upward with the force of the blow, so that the edge of the cup will ride-up on the scrotum and impact the testes. As a result, the cup itself can cause considerable injury or at least pain, contrary to its intended purpose.

My prior U.S. Pat. No. 4,043,329, issued Aug. 23, 1977, disclosed an improved cup having a narrow, rearwardly protruding portion at the lower edge designed to protrude inwardly between the upper thighs, and engage the superior ramii, the inferior ramii and the Ischial ramii of the pelvis, to thereby prevent any upward movement of the cup as a result of upwardly directed blows. The patented cup has enjoyed significant commercial success, particularly in the field of martial arts, and other contact sport activities, such as football, baseball and soccer. Despite the success of the patented cup, however, there have been situations where it has not provided the optimum degree of protection as would be desired, nor has it provided optimum comfort. For example, prior art cups are all designed to provide a generally straight and horizontal upper edge which intersects the slightly angled, vertical side edges to form a corner. Although the corners are usually well rounded, the width of the cup at the top near the rounded corners, is normally the overall widest dimension of the cup. When the cup is impacted at an angle, the cup can be forced to twist, thereby forcing a rounded corner into the abdomen at the groin region. While this is not only somewhat painful, it can cause physical damage to the groin region.

In addition to the above short-comings, the protective cups of the prior art are all rather uncomfortable to the wearer in several respects. For example, the prior art cup geometry has been generally V-shaped in form with generally angled side edges coming together at the lower end to avoid contact with the upper thighs, with the result that the male genitals may be rather crowded within the cup, not only causing a crowded uncomfortable feeling, but further reducing ventilation through the cup which results in excessive perspiration and moisture build-up. With regard to my previously patented cup, on the other hand, the rearwardly protruding portion is too wide adjacent to the cup portion, thereby causing the thighs to rub against the edges of the cup, which is not only uncomfortable, but may cause skin abrasion if allowed to persist for a period of time.

As another example of the short-comings of the prior art cups, there have been situations where a particular blow to the protective cup has been so sharp and forceful, that the cup has been fractured. Even if the cup does not fracture, if the athlete's testes are positioned so as to be in contact against an inside surface of the cup, a forceful, sharp blow against the outside surface, such as a carelessly swung baseball bat, will often be quite painful, even if not causing any actual physical injury. If the cup is caused to fracture, continued athletic activity with a fractured cup will not only risk injury as the cup may fail to provide the protection intended, but the fractured fragments of the cup can themselves cause significant injury to the groin region as a result of jagged fracture edges on such fracture fragments. Even slightly cracked cups can cause significant pain if flesh gets pinched within a closely spaced fracture crack.

With regard to the prior art cup supporters, it would appear that very little thought has been given thereto. Such cup supporters are usually designed to be substantially identical to conventional athletic supporters or jockstraps, the front panel of which has two layers so as to form a pouch for containing the cup. The top end of the two layered front panel is left open to permit an opening through which the cup can be inserted and removed. Such prior art cup supporters are known to do little to stabilize and maintain the cup in its proper position, and when impacted with an upwardly directed blow, the cup can be pushed upward through the top opening and be dislodged partially, and even completely, from the cup supporter pouch. When the cup is even partially dislodged from the pouch, it will not afford the degree of protection intended, and will normally require the athlete to exit the playing field or arena to replace and reposition the cup and cup supporter.

SUMMARY OF THE INVENTION

This invention is predicated upon a new and improved protective system including both a protective cup and a cup supporter for the protection of the male groin region, particularly during athletic activities, such as contact sports, which will not only provide superior protection to the male genital region as a result of improved cup geometry, but further provided a greater degree of comfort to practically any wearer. In addition, an optional interior cup padding can be provided to prevent the groin region from direct contact with the interior surface of the cup itself for enhanced protection, as well as reinforcing to provide superior fracture resistance as compared to cups of the prior art.

With regard to the cup supporter, this invention provides a cup supporter having reinforced leg straps to better stabilize the cup in its intended position and an access opening through which the cup cannot be forced out by virtue of normal athletic activity.

While most of the unique features of the inventive cup can be incorporated into any prior art cup, the preferred embodiment of the cup of this invention is a significantly improved version of my protective cup as disclosed in my above-identified U.S. Pat. No. 4,043,329, so as to incorporate the extra protection afforded by both inventions.

In essence, the protective cup of this invention is a cup having a generally convex outer surface, a generally concave inner surface and having sufficient volume to enclose a wearer's male genitals. As in the case of all prior art cups, a resilient edge padding is mounted on the edge of the cup adequate to contact the a wearer's body around the groin region and absorb at least a portion of any frontal impact experienced by the cup. Preferably the cup also has a rearwardly extending lower portion, or support rod, adapted to extend between the wearer's upper thighs and engages his body proximate to the superior ramii, the inferior ramii, and/or the Ischial ramii of the pelvis with minimal contact with the upper thighs, substantially as disclosed in my above-mentioned prior U.S. patent. This feature will protect the groin region from upwardly directed blows by preventing the force of the blow from moving the cup upwardly. Unlike prior art cups, however, the cup of this invention is provided with a rounded upper edge adapted to arcuately contact the wearer's abdomen above the pubic area without having any outwardly extending corner intersections, rounded or otherwise, between the generally vertical side edges and the generally horizontal upper edge of the cup; and in addition, a generally circular periphery at a mid-section below the generally curved upper edge, is provided which is adapted to enclose the wearer's genitals without crowding such genitals. As a preferred option, the inventive cup can further include a resilient inner padding secured, permanently or removably, adjacent to the interior concave surface of the cup adequate to prevent the male genitals from direct contact with the inner surface of the cup. It is also preferable that the cup have a blunted edge under the edge padding for the purpose of eliminating the placement of a thin cup edge perpendicularly against the wearer's body. In a similar vein, the resilient edge padding mounted on the edge of the cup is preferably provided with a continuous flattened side surface adapted to enhance the area of contact against the wearer's body. To enhance fracture resistance, the convex outer surface of the cup is preferably provided with a molded-in grid work to add structural reinforcement.

With regard to the cup supporter of this invention, the leg straps are not only reinforced, but repositioned to greatly enhance the stability of the cup holding pouch, while the cup access opening is improved to prevent any normal force from pushing the cup from the pouch during normal athletic activity.

OBJECTS OF THE INVENTION

Accordingly, the primary object of this invention is to provide a new and improved protective system for protecting the male genital region from injury, particularly during athletic competition, including a new and improved protective cup and a new and improved cup supporter, the combination of which not only provides superior protection as a result of improved cup geometry, but is more comfortable to wear, and further includes a cup supporter that better retains the cup in its intended position.

Another primary object of this invention is to provide a new and improved geometry for a protective cup for protecting the male genital region from injury which not only provided superior protection, but also improved comfort.

Another primary object of this invention is to provide a new and improved protective cup for protecting the male genital region from injury which includes a resilient padding adjacent to the interior surface of the cup to shield the genitals, and particularly the testes, from direct contact with the interior cup surface to save the wearer from pain when the cup is subjected to a sharp impact.

Still another object of this invention is to provide a new and improved protective cup for protecting the male genital region from injury which is provided with a generally curved upper edge adapted to arcuately contact the abdomen above the pubic area without having any outwardly extending corner intersections between the side edges and the upper edge of the cup.

A further object of this invention is to provide a new and improved protective cup for protecting the male genital region from injury having a generally circular periphery at a mid-section below the generally curved upper edge adapted to enclose the wearer's genitals without crowding such genitals.

An additional object of this invention is to provide a new and improved protective cup for protecting the male genital region from injury which is provided with a blunted edge under the edge padding for the purpose of eliminating placement of a narrow cup edge perpendicularly against the wearer's body.

An even further object of this invention is to provide a new and improved protective cup for protecting the male genital region from injury in which the resilient padding mounted on the edge of the cup is provided with a continuous flattened side surface adapted to enhance the area of contact against the wearer's body to distribute any impact loads over a greater area.

A still further object of this invention is to provide a new and improved protective cup for protecting the male genital region from injury in which the outer surface is provided with a molded-in grid work for the purposes of adding structural reinforcement to increase the cup's fracture resistance.

Yet another object of this invention is to provide a new and improved cup supporter for maintaining the inventive cup in its intended position which provides improved leg strap supports which better stabilize the cup both vertically and horizontally.

An even further object of this invention is to provide a new and improved cup supporter for maintaining the inventive cup in its intended position which provides an improved pouch opening which better retains the cup within the pouch.

These and other objects and advantages of this invention will become apparent from a better understanding of the following detailed description of the invention.

BRIEF DESCRIPTION OF THE DRAWINGS

FIG. 7 is an enlarged sectional view of the resilient padding mounted on the edge of the cup showing one embodiment of the preferred flattened side surface of the edge padding, and one embodiment of the blunted edge of the cup.

FIG. 8 is another enlarged sectional view of the resilient padding mounted on the edge of the cup showing another embodiment of the preferred flattened side surface of the padding, and another embodiment of the blunted edge of the cup.

FIG. 9 is still another enlarged sectional view of the resilient padding mounted on the edge of the cup showing still another embodiment of the preferred flattened side surface of the padding and still another embodiment of the blunted edge of the cup.

FIG. 10, is an enlarged view of a portion of a cup edge showing holes therethrough as utilized to better bond an edge padding to the cup edge.

FIGS. 11 and 12 are like FIG. 10 showing recesses into the edge surface rather than holes, which can be utilized to better bond an edge padding to the cup edge.

DESCRIPTION OF THE PREFERRED EMBODIMENTS OF THE INVENTION

Figure 1:
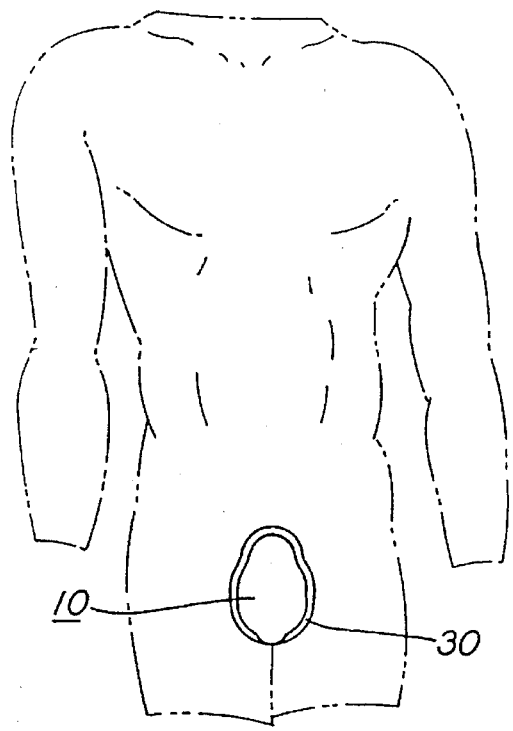
FIG. 1 is a front view of a protective device in accordance with a preferred embodiment of this invention showing its intended position when worn by a man.
Figure 2:
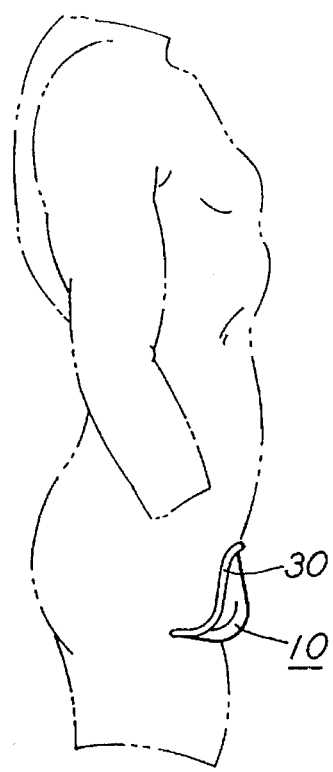
FIG. 2 is a side view of the illustration shown in FIG. 1.
Figure 3:
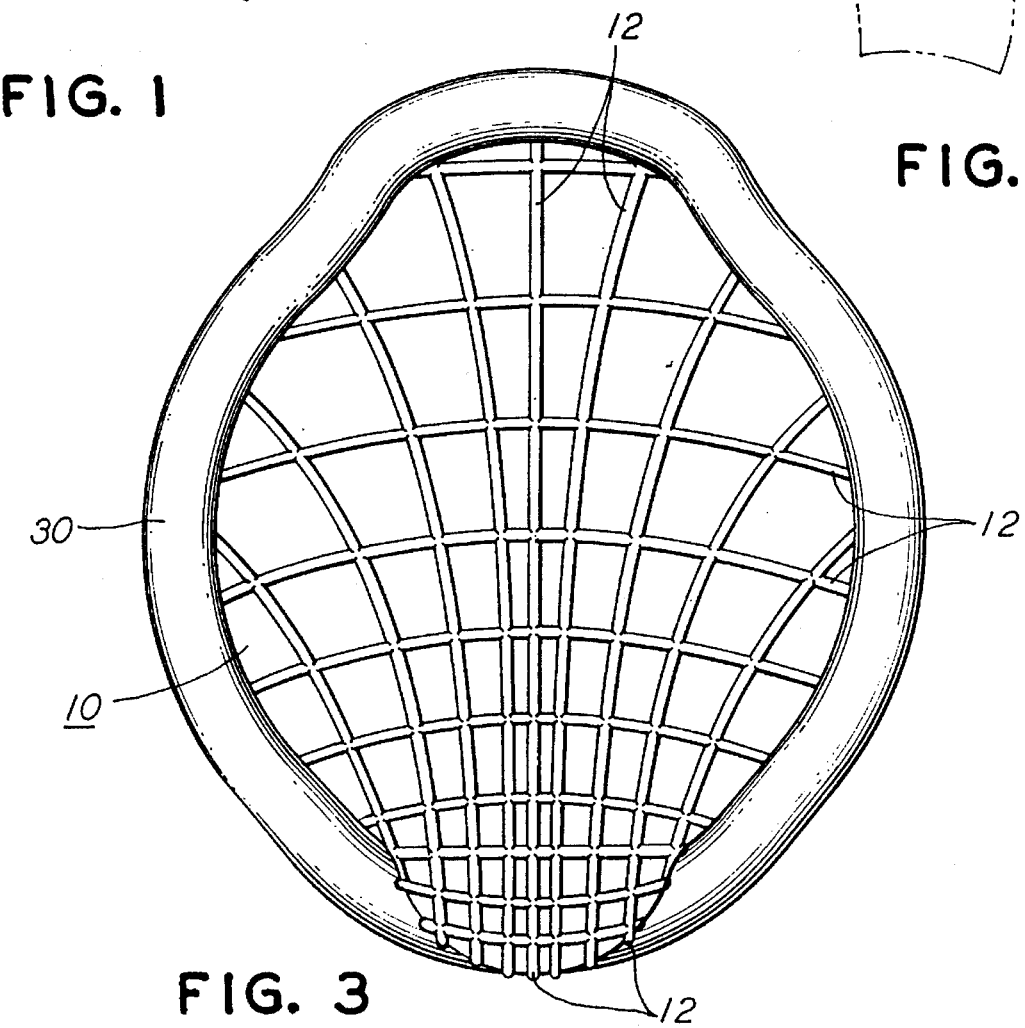
FIG. 3 is a front view of the cup shown in FIGS. 1 and 2 showing the preferred molded-in strengthening grid work.
Figure 4:
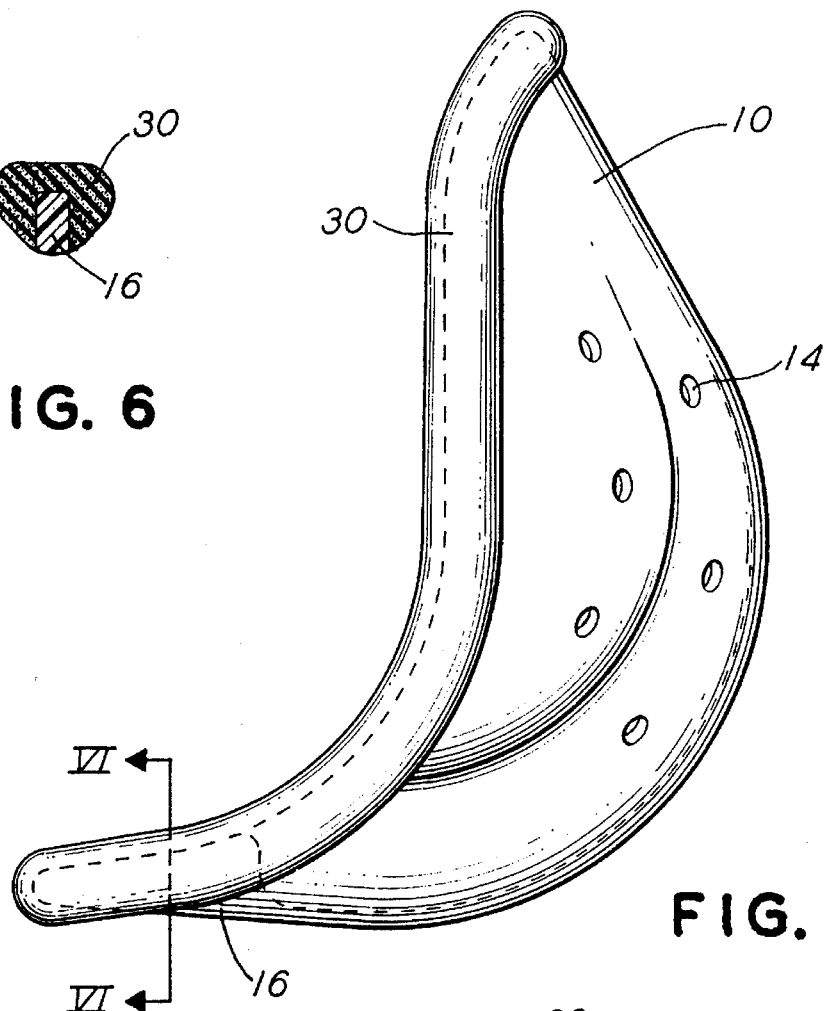
FIG. 4 is a side view of the cup shown in FIGS. 1–3, which for purposes of simplicity does not illustrate the molded-in grid work.

Prior to proceeding with a detailed description of the subject invention, it is noted that for the sake of clarity, identical components which have identical functions have been identified with identical reference numerals throughout the several views of the attached drawings.

Reference to FIGS. 1–6 will illustrate one presently preferred embodiment of the protective cup 10 of this invention, wherein the front portion, or cup portion, has a generally convex outer surface, a generally concave inner surface and a sufficient volume to enclose a wearer's male genitals, and a support rod portion 16. As shown in the FIG. 3 embodiment of the invention, the convex outside surface of the cup 10 is preferably provided with a grid of reinforcing, protruding ribs 12 extending from the smooth outer surface of cup 10. While the grid of ribs 12 can be arranged in any desired pattern, such as a rectangular pattern, a preferable arrangement is a contoured parabolic arrangement, as shown, which concentrates the ribs 12 at the maximum protruding apex of the surface for maximum reinforcing affect. While placement of such ribs 12 on the concave inside surface of the cup 10 would provide some additional benefit as compared to the outside surface alone, such ribs 12 positioned on the inside surface could be a source of irritation to the wearer's genitals, and are therefore not preferred. Indeed, it is believed that the reinforcing ribs 12 on the outside surface of the cup alone will be more than adequate to provide the degree of fracture resistance needed.

A plurality of apertures 14 are normally provided through cup 10 to afford ventilation to the groin area. Although the apertures 14 are not necessary for protection of the genitals and the area associated therewith, the ventilation will render the protective device more comfortable during prolonged wear, at least, in minimizing perspiration and the accumulation of moisture.

Figure 6:
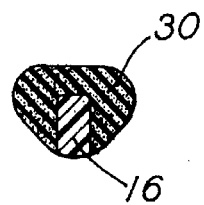
FIG. 6 is a cross-sectional view of the cup portion, or support rod extending between the wearer's upper thighs taken at line VI—VI of FIGS. 4 and 5.
Figure 5:
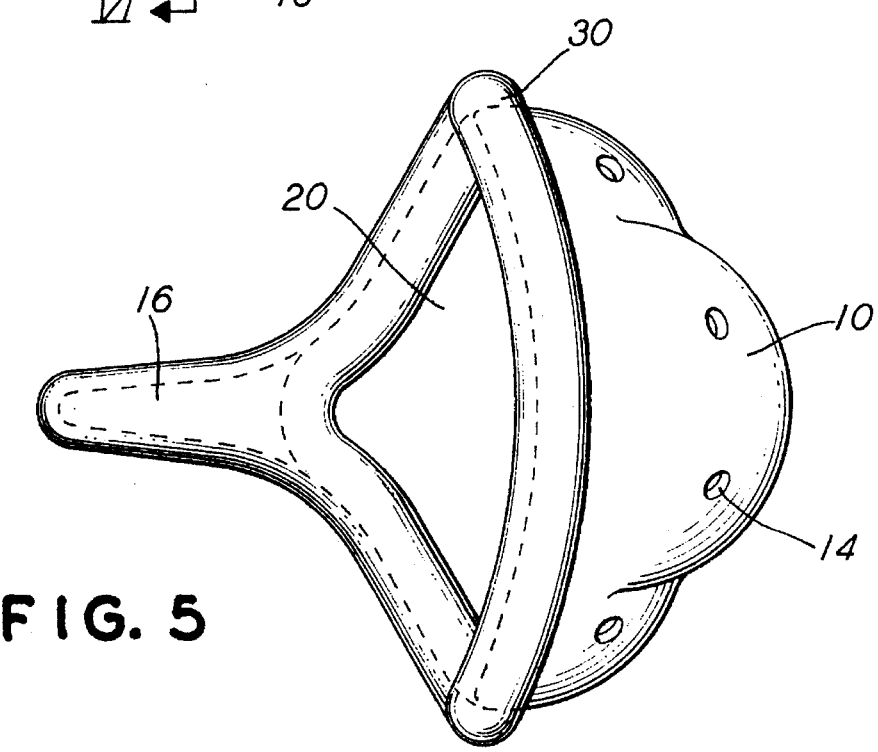
FIG. 5 is a top view of the cup shown in FIGS. 1–4, which again, for purposes of simplicity, does not illustrate the molded-in grid work.

As previously noted, the front, or cup portion, of the cup 10 should have sufficient volume to contain the male genitals, and the support rod portion 16 portion need not have any volume, but should merely comprise a narrow finger-like extension 16 designed to extend between the wearer's upper thighs, and engage his body proximate to the superior ramii, the inferior ramii, and/or the Ischial ramii of the pelvis with minimal contact with the upper thighs. While this concept was disclosed in my above-said U.S. patent, the finger-like extension 16 on the cups produced under the patent were shorter and wider than shown in those patent drawings, and subsequently found to be too short and too wide for optimum comfort, at least in the forward portion. Indeed, the support rod portion 16 should be as narrow as possible to assure minimal contact with the upper thighs and thereby minimize any irritating frictional contact with the upper thighs when the wearer is walking or running. Contrary to the drawings in my prior patent, however, the extension rod 16 should preferably have a larger dimension in the vertical direction as opposed to the horizontal direction, as shown in FIG. 6. This will not only serve to add strength to extension rod 16 where it is most needed, namely in the vertical direction to resist bending and fracture when hit with an upwardly directed blow but will further serve to reduce width and thereby minimize the possibility for abrasive contact against the upper thighs.

The top end of the cup 10; is preferably rounded or curved, as shown, and adapted to arcuately contact the wearer's abdomen above the pubic area without having any corner intersections between the side edges and the top edge of the cup 10. If the cup 10 is impacted at an angle and forced to be twisted, there are no corners, rounded or otherwise, at the top of the cup portion 10 to be forced into the wearer's abdomen. The mid-section of the cup 10, immediately below the rounded upped edge, should be wider than the top edge to assure enclosing the wearer's genitals without crowding such genitals. Ideally, this mid-section should have generally circular edge peripheries adapted to contact the wearer's abdomen on each side of the pubic area.

For optimum protection, cup 10 is preferably formed of a substantially rigid plastic material of construction such as polypropylene, high density polyethylene or similar material sufficiently rigid so that the cup 10 will retain its shape when impacted. Although virtually any substantially rigid plastic material may be used in the construction of cup 10, care must be taken to insure that the plastic material is sufficiently strong and tough to minimize the possibility of fracture or deformation when impacted and sufficiently inert to possess no irritating characteristics that can cause skin irritation or rashes. While in one embodiment of the invention, the cup 10 is extruded from Hercules GR1 extrusion grade polypropylene, it should be apparent that the cup 10 may be extruded, vacuum formed, molded or otherwise formed by any suitable process, utilizing any suitable rigid material, including metal. While rigid or substantially rigid materials are preferred for purposes of assuring adequate protection in the more threatening situations, it should be appreciated that less than rigid material, such as a shaped stiff fabric material, can be utilized for situations where there is no probability of any particularly forceful blows to the groin region. Accordingly, it is not intended that the cup of this invention be limited to fabrication from any given type of material.

A sheet of resilient face padding 20, is preferably provided adjacent to the concave inside surface of cup 10 to space the male genitals from direct contact with such inner surface of the cup 10. Such face padding 20 should be made of a relatively soft resilient material such as foam rubber or a sponge-like material, so that a sharp impact against the outside surface of cup 10 will not be transferred to the male genitals. While the sheet of resilient face padding 20 can be bonded directly onto the interior surface of cup 10, it may be preferred that it be held in place at the edge of the cup 10 by the edge padding 30 so that it is stretched from one side to the other without being in direct contact with the midportion of the cup 10. In this way, the genitals can be held and cupped by the padding 20, in a manner akin to that of a jockstrap, spaced from contact with the hard surface of the cup 10. Depending upon the porosity of the material utilized for the resilient face padding 20, a plurality of apertures may or may not be necessary to facilitate ventilation to the groin area. While apertures in face padding 20 need not be aligned with the apertures 14 in cup 10, such alignment could be beneficial if face padding 20 is directly bonded to the inner surface of cup 10.

As on conventional prior art cups, a resilient edge padding 30 is mounted around the edge of cup 10 and is adapted to contact the wearer's lower body and absorb a major portion of the impact experienced by the cup 10. The resilient edge padding 30 is preferably foamed of natural rubber, or flexible polyurethane foam. In one embodiment of the invention, the resilient padding 30 is Craton Polyfoam flexible foam. Although the resilient edge padding 30 will protect the wearer somewhat when the edge of the cup 10 driven against his lower body, is should be appreciated that the edge padding 30 is resilient and will be compressed around the narrow edge of the cup 10 when driven against the wearer's body with appreciable force. When so compressed, the narrow edge of the cup 10 can nevertheless cause some pain and damage particularly as a result of particularly forceful blows or repeated blows to the cup 10. Therefore, a preferred embodiment of this invention is one where the edge of the cup 10 is blunted by incorporating a rounded bead 18a, a small right-angle flange 18b or a small "T" flange 18c, as shown in FIGS. 7, 8 and 9, adapted to present a widened flat or rounded edge against the wearer's body, to enhance the surface area of the cup edge oriented towards the wearer's body. In this way, even particularly forceful blows to the cup 10, which will compress the edge padding 30 against the edge of the cup 10, will not expose the wearer's body to the normally narrow edge of the cup 10. By eliminating the conventional edge on the cup 10, it can be seen that there will be less tendency for the edge of the cup 10 to cut through the edge padding 30 and thereby loosen it from the cup 10.

In a like manner, it is also preferred that the resilient edge padding 30 itself have a continuous, flattened surface 32 positioned such that the flattened surface 32 will mate with the surface of the wearer's body. This will not only serve to reduce any pain or discomfort to the wearer in the event of a forceful blow to the cup 10, but will serve to enhance the bonding force against the blunted cup edge as described above.

The resilient edge padding 30 is generally tubular or cylindrical in form having a slit herein for mounting on the edge of cup 10 with an adhesive, or in the alternative is cylindrical in form cast and molded directly onto the cup edge. In either event, such edge padding 30 can become loosened from the cup edge to the extent that the cup 10 becomes useless for its intended purpose. The inclusion of a blunted edge on the cup 10 as disclosed above, particularly in combination with a flattened surface on the edge patting 30, as described above, will also serve to improve any bonding between the edge padding 30 and the cup edge. If necessary to further enhance the bonding effect, the edge of the cup 10 could be provided with a plurality of transverse holes 19a, through the side face of the cup 10, or angled recesses 19b, as shown in FIGS. 10, 11 and 12, which would serve to form anchors to an edge padding 30 molded onto the edge of a cup 10. If desired the resilient padding 30 may be covered with a sheet or layer of thin plastic 34 such as vinyl polyethylene of the like.

Figure 13:
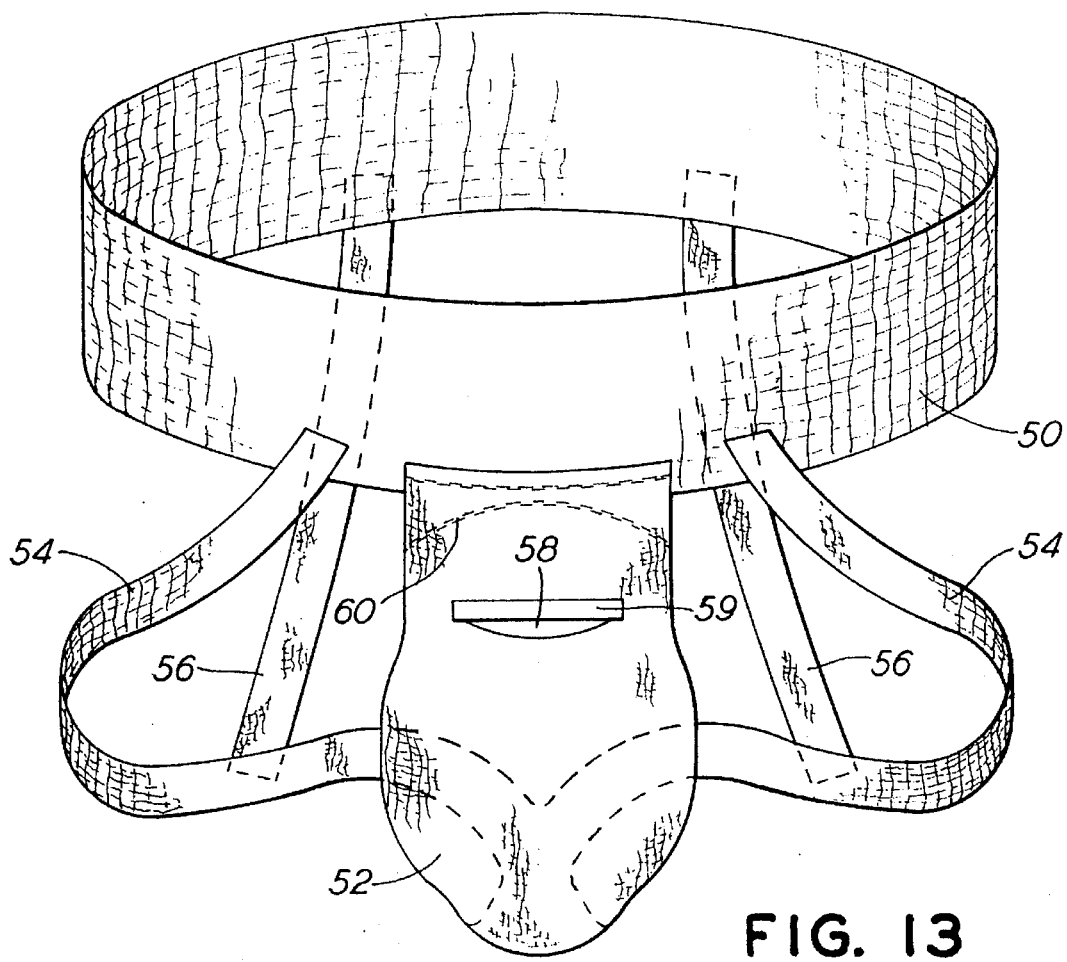
FIG. 13 is a front isometric view of the inventive cup supporter in accordance with one embodiment of this invention.

Although the protective cup 10 may be mounted to the body by straps or by any conventional prior art supporter having a pouch adapted to receive a cup, a superior protective system can be achieved by utilizing the above disclosed cup 10 in combination with an improved supporter means in accordance with additional embodiments of this invention. Specifically, one presently preferred embodiment of the new and improved supporter according to this invention is illustrated in FIG. 13 and comprises an elastic waist band 50, having a generally elastic-fabric pouch 52 attached to the center-front of the waist band 50 adapted to extend downwardly over the male genitals. One end each of a pair of elastic leg straps 54 is attached to the lower end of pouch 52 with the opposite end of each leg strap 54 attached to the front of waist band 50 preferably adjacent to where the top edge of pouch 52 is attached. The elastic leg straps 54 are accordingly intended to extend tightly from the bottom of pouch 52, positioned between the wearer's upper thighs, and extend upwardly and outwardly across the top extremity of each thigh, and accordingly over the hips to reengage the waist band 50 at the front. An elastic support strap 56 is also provided for each elastic leg strap 54, one end of which is attached to approximately the mid-length of the associated leg strap 54, and extend diagonally upwardly across each side of the buttocks and attached to the waist band 50, generally opposed to the point where each leg strap 54 is attached at the front. Accordingly, this presently preferred arrangement serves to provide both vertical and lateral support for the cup 10, greatly preventing the possibility that any blow will displace the cup 10 from its intended position.

The fabric pouch 52 should obviously be adapted to contain cup 10, having a front layer and a rear layer, and should have an opening 58 through which the cup 10 can be inserted. While prior art practice has been to leave an opening at the top of the pouch between the two layers through which the cup can be inserted, the cup supporter of this invention is provided with an opening 58 in either one of the two pouch layers displaced downwardly from the upper edge of an inserted cup, for the purpose of leaving a portion of the interior pouch, and the inserted cup, above the opening. In this way, the top edge of cup 10 will be positioned within the pouch 52 above opening 58, so that this top portion of the pouch 52 serves to contain the upper portion of cup 10 within the area displaced from the opening 58. Accordingly, any upwardly directed blows or forces against the cup 10 cannot drive the cup 10 out through the opening 58, but rather the cup 10 will be forced to stay within the pouch 52. As an extra precaution in this regard, it is preferred that the opening 58 be an elongated slot-type opening having a width somewhat smaller than the width of cup 10, so that opening 58 will have to be stretched in order to fit cup 10 into and out of the pouch, and also that the opening 58 be defined by a pair of flat elastic bands 59, one overlaying the other, thereby making it more unlikely that the cup 10 will be pushed from the pouch unintentionally. As an alternative, the slot-type opening 58 can be provided with a zipper which will serve to lock the cup 10 into the pouch 52.

In order to keep the cup 10 properly positioned with regard to the supporter, the pouch 52 should have a configuration as necessary to closely match the configuration of the cup 10, to thereby prevent the cup 10 from moving around within the pouch 52. As shown in FIG. 13, a curved line of stitching 60 is provided at the upper end of pouch 52 as necessary to define a curved upper end of pouch 52 to mate with the curved upper edge of cup 10. Accordingly, the closely confining pouch 52 will keep the cup 10 properly positioned therein, and the unique strap arrangement as disclosed above, will keep the pouch 52 properly stabilized during activity so that the cup 10 will be maintained in its proper position regardless of the wearer's activity and blows directed to the cup 10.

Figure 14:
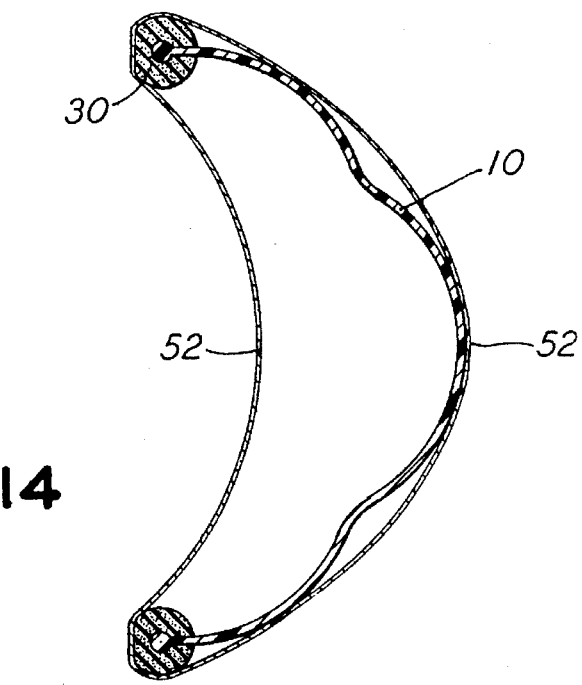
FIG. 14 is a cross-sectional view through the pouch portion of the supporter shown in FIG. 13, having a cup therein and illustrating a preferred embodiment wherein the inside portion of the pouch is stretched across the concave inner portion of the cup.

In a preferred embodiment of the cup supporter of this invention, pouch 52 should be produced so as to allow a sufficient surface area of fabric at the outside to naturally accommodate the outer, convex portion of the cup 10, while a reduced amount of fabric is provided on the inside so that the inside portion of the pouch 52 is caused to be at least somewhat stretched across the inner convex portion of cup 10, substantially as shown in FIG. 14. In this way, the stretched inside portion of the pouch 52 will serve to elastically hold the male genitals away from the cup 10, and further prevent contact of the genitals with the inside surface of cup 10. Ideally, the inside surface of pouch 52 should not be stretched taught so as to restrict or confine access to the cavity of the cup 10, but stretched only tight enough to form a fabric cup to cradle the male genitals and keep them spaced from the hard inner surface of cup 10.

Having shown and described several embodiments of the invention above, it should be readily apparent that a great number variations could be made without departing from the spirit of the invention. While no dimensions or sizing has been described above, it should be appreciated that the cup and cup supporter can be made available in differing sizes not only to accommodate adult, youth and child sizes, but to accommodate varying sizes in each group.

I claim:

1. A device for protecting a male genital region from injury comprising: a cup portion having a generally convex outer surface, a generally concave inner surface, an edge encircling said concave inner surface, and having sufficient volume to enclose a wearer's male genitals; a resilient edge padding mounted over said edge encircling said concave inner surface adequate to contact such wearer's body at the lower portion thereof and absorb at least a major portion of any impact experienced by said device; and a support rod extending from a lower portion of said edge generally away from said concave inner surface, and adapted to extend between such wearer's upper thighs and engage the body proximate to the superior ramii, the inferior ramii, and/or the Ischial ramii of the pelvis with minimal contact with the upper thighs; said cup portion further having;

a. a generally curved upper edge adapted to arcuately contact the wearer's abdomen above the pubic area without having any corner intersections between side edges and a top edge of said cup, and b. a generally circular side edge periphery at a mid-section below said generally curved upper edge adapted to contact the wearer's abdomen on each side of the pubic area and enclose the wearer's genitals without crowding such genitals.

2. A device for protecting a male genital region from injury, according to claim 1, in which a resilient face padding is provided adjacent to said concave inner surface of said cup portion adequate to prevent the male genitals from direct contact with said cup portion.

3. A device for protecting a male genital region from injury, according to claim 2, in which said resilient face padding is removably secured adjacent to said concave inner surface of said cup portion.

4. A device for protecting a male genital region from injury, according to claim 1, in which said convex outer surface of said cup portion is provided with a grid work of reinforcing ridges.

5. A device for protecting a male genital region from injury, according to claim 4, in which said grid work of ridges is arranged in a contoured parabolic arrangement.

6. A device for protecting a male genital region from injury, according to claim 1, in which said edge encircling said concave inner surface is blunted sufficient to eliminate placement of a narrow cup edge perpendicularly against the wearer's body.

7. A device for protecting a male genital region from injury, according to claim 6, in which said blunted outer edge comprises a generally cylindrical bead.

8. A device for protecting a male genital region from injury, according to claim 6, in which said blunted outer edge comprises a flange.

9. A device for protecting a male genital region from injury, according to claim 1, in which said resilient edge padding mounted on the edge of said cup is provided with a continuous, generally flattened side surface such that said continuous flattened surface is adapted to be in contact against the wearer's body.

10. A cup supporter for holding a cup for protecting a male genital region from injury comprising: an elastic waist band having front and back portions and adapted to fit snugly around a wearer's waist; a fabric pouch attached to said front portion of said waist band and adapted to extend downwardly over such wearer's male genitals, said pouch having an opening through which such cup can be inserted; a pair of elastic leg straps, one end of each said leg straps attached to a lower end of said pouch with the opposite end of each said elastic leg strap attached to the front of said waist band adjacent to said pouch, said elastic leg straps adapted to extend from the bottom of said pouch between the wearer's upper thighs, and extend upwardly and outwardly across the top extremity of each thigh, over the hips and to said front portion of said waist band; and a pair of elastic support straps, one end of each said support straps attached to the approximate mid-length of one each of said elastic leg straps and the other end of each said support strap attached to said back portion of said waist strap, each of said support straps adapted to extend diagonally upwardly across one side of the buttocks.

11. A cup supporter for holding a cup for protecting a male genital region from injury, according to claim 10, in which said pouch opening comprises an elongated slit having a width smaller than the width of such cup, and said opening positioned sufficiently below said waist band that such cup will be partially positioned within said pouch above said opening.

12. A cup supporter for holding a cup for protecting a male genital region from injury, according to claim 11, in which said elongated slit opening comprises a pair of overlaying elastic strips with said opening being parallel to said pouch between said overlaying elastic strips.

13. A cup supporter for holding a cup for protecting a male genital region from injury, according to claim 11, in which said elongated slit opening is provided with a zipper.

14. A cup supporter for holding a cup for protecting a male genital region from injury, according to claim 11, in which said pouch has an excessive amount of fabric at an outside portion adapted to naturally accommodate the convex portion of such cup, and a reduced amount of fabric on an inside portion such that said inside portion of said pouch is caused to be stretched across the inside convex portion of such cup.

15. A cup system for protecting a male genital region from injury comprising:

a cup supporter having an elastic waist band having front and back portions and adapted to fit snugly around a wearer's waist; a fabric pouch attached to said front portion of said waist band and adapted to extend downwardly over such wearer's male genitals, said pouch having an opening through which such cup can be inserted; a pair of elastic leg straps, one end of each said leg straps attached to a lower end of said pouch with the opposite end of each said elastic leg strap attached to the front of said waist band adjacent to said pouch, said elastic leg straps adapted to extend from the bottom of said pouch between the wearer's upper thighs, and extend upwardly and outwardly across the top extremity of each thigh, over the hips and to said front portion of said waist band; and a pair of elastic support straps, one end of each said support straps attached to the approximate mid-length of one each of said elastic leg straps and the other end of each said support straps attached to said back portion of said waist strap, each of said support straps adapted to extend diagonally upwardly across one side of the buttocks; and a cup having a generally convex outer surface, a generally concave inner surface, an edge encircling said concave inner surface, and having sufficient volume to enclose a wearer's male genitals, said cup having a support rod extending from a lower portion of said edge generally away from said concave inner surface, and adapted to extend rearwardly between such wearer's upper thighs and engage the body proximate to the superior ramii, the inferior ramii, and/or the Ischial ramii of the pelvis with minimal contact with the upper thighs; said cup portion further having;

a. a generally curved upper edge adapted to arcuately contact the wearer's abdomen above the pubic area without having any corner intersections between side edges and a top edge of said cup, and b. a generally circular side edge periphery at a mid-section below said generally curved upper edge adapted to contact the wearer's abdomen on each side of the pubic area and enclose the wearer's genitals without crowding such genitals.

16. A cup system for protecting a male genital region from injury, according to claim 15, in which a resilient face padding is provided adjacent to said concave inner surface of said cup portion adequate to prevent the male genitals from direct contact with said cup portion.

17. A cup system for protecting a male genital region from injury, according to claim 16, in which said resilient face padding adjacent to said concave inner surface of said cup is provided by an inside surface of portion of said fabric pouch attached to said front portion of said waist band adapted to be stretched tightly over said concave portion of said cup.

18. A cup system for protecting a male genital region from injury, according to claim 15, in which said convex outer surface of said cup is provided with a grid work of reinforcing ridges.

19. A cup system for protecting a male genital region from injury, according to claim 15, in which said edge of said cup is blunted sufficient to eliminate placement of a narrow cup edge perpendicularly against the wearer's body.

20. A cup system for protecting a male genital region from injury, according to claim 15, in which said resilient edge padding mounted on the edge of said cup is provided with a continuous flattened side surface such that said continuous flattened surface is adapted to be in contact against the wearer's body.

\* \* \* \* \*

UNITED STATES PATENT AND TRADEMARK OFFICE
CERTIFICATE OF CORRECTION

PATENT NO. : 5,479,942
DATED : Jan. 2, 1996
INVENTOR(S) : Frank DiMatteo

It is certified that error appears in the above-indentified patent and that said Letters Patent is hereby corrected as shown below:

Column 1, line 50, delete "my" and insert --may--.
Column 3, line 26, delete "a".
Column 7, line 27, delete "midportion" and insert --mid-portion--;
column 7, line 42, delete "foamed" and insert --formed--;
column 7, line 47, delete "is" and insert --it--.
Column 8, line 17, delete "patting" and insert --padding--.

Signed and Sealed this

Twenty-eighth Day of May, 1996

Attest:

BRUCE LEHMAN

*Attesting Officer*    *Commissioner of Patents and Trademarks*